(12) United States Patent
Tefera et al.

(10) Patent No.: US 8,968,242 B2
(45) Date of Patent: Mar. 3, 2015

(54) INFLATABLE ELASTOMERIC PUMP FOR AN INFUSION ASSEMBLY

(71) Applicant: Avent, Inc., Alpharetta, GA (US)

(72) Inventors: Kokeb Tefera, Lake Forest, CA (US); Quang Ngoc Vu, Aliso Viejo, CA (US); Deepak Gandhi, Irvine, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 13/755,037

(22) Filed: Jan. 31, 2013

(65) Prior Publication Data

US 2013/0211333 A1    Aug. 15, 2013

Related U.S. Application Data

(60) Provisional application No. 61/637,963, filed on Apr. 25, 2012, provisional application No. 61/616,589, filed on Mar. 28, 2012, provisional application No. 61/597,502, filed on Feb. 10, 2012.

(51) Int. Cl.
*A61M 37/00* (2006.01)
*A61M 5/145* (2006.01)
*A61M 5/152* (2006.01)

(52) U.S. Cl.
CPC .............. *A61M 5/145* (2013.01); *A61M 5/152* (2013.01); *A61M 2205/0216* (2013.01)
USPC ........................................... 604/132; 604/153

(58) Field of Classification Search
USPC .................. 604/131–133, 140, 142, 151–153
See application file for complete search history.

(56) References Cited

U.S. PATENT DOCUMENTS

| | | | |
|---|---|---|---|
| 3,993,069 A * | 11/1976 | Buckles et al. | 604/132 |
| 4,909,790 A | 3/1990 | Tsujikawa et al. | |
| 5,105,983 A | 4/1992 | Sancoff et al. | |
| 5,178,610 A * | 1/1993 | Tsujikawa et al. | 604/132 |
| 5,284,481 A | 2/1994 | Soika et al. | |
| 5,529,214 A * | 6/1996 | Lasonde et al. | 222/105 |
| 7,704,230 B2 * | 4/2010 | Chatlynne et al. | 604/132 |
| 2004/0138627 A1 | 7/2004 | Forrest | |

FOREIGN PATENT DOCUMENTS

| | | |
|---|---|---|
| EP | 0 426 319 A2 | 5/1991 |
| EP | 0 452 912 A2 | 10/1991 |
| EP | 0 542 401 A1 | 5/1993 |
| EP | 1 086 715 A2 | 3/2001 |
| GB | 1 454 310 A | 11/1976 |

* cited by examiner

*Primary Examiner* — Laura Bouchelle
(74) *Attorney, Agent, or Firm* — Dority & Manning, P.A.

(57) ABSTRACT

An improved elastomeric pump for an infusion assembly. The pump includes a generally cylindrical mandrel body with first end, an opposed second end, a length, an outer diameter corresponding to a first radius ($R_{mandrel}$), a central bore extending through the length, a first port extending from the outer diameter to the bore to provide a fluid passageway, a fill port and an exit port in fluid communication with the bore. The pump includes an inflatable elastomeric tube disposed concentrically about the mandrel, the tube being sealingly secured on the mandrel near the respective ends of the tube and having an original inner diameter that corresponds to a second radius (r) so that it approximately matches the outer diameter of the mandrel ($R_{mandrel}$), a length (L) less than the length of the mandrel, a wall thickness (t) such that:

$(0.4225 \times r) < t \leq (0.660 \times r)$.

14 Claims, 6 Drawing Sheets

INFLATABLE ELASTOMERIC PUMP FOR AN INFUSION ASSEMBLY

This application claims the benefit of priority from U.S. Provisional Applications No. 61/637,963 filed on Apr. 25, 2012 and from No. 61/616,589 filed on Mar. 28, 2012 and from No. 61/597,502 filed Feb. 10, 2012.

FIELD OF THE INVENTION

The present invention relates to liquid dispensing apparatus and pertains particularly to an improved infusion apparatus or assembly for delivering intravenous drugs at a controlled rate to a patient.

BACKGROUND OF THE INVENTION

It is often necessary to intravenously supply patients with pharmaceutically active liquids at a controlled rate over a long period of time. It is desirable that this be accomplished while the patient is in an ambulatory state. A few devices have been developed in the past for accomplishing this purpose.

The prior art devices typically include an inflatable elastomeric bladder forming a liquid container and have a flow control valve or device and tubing for supply of the liquid to the patient. The walls of the bladder are forced to expand when filled with the liquid, and provide the pressure for expelling the liquid. These prior art devices are typically filled by hand by means of a syringe which often require an inordinate amount of force.

Another drawback to the prior art devices is that the conventional inflatable elastomeric bladder provides pressures and flow rates that can vary widely with the volume of liquid therein. Therefore, they do not have a reasonably stable pressure and flow rate over the infusion period. In addition, such conventional bladders frequently have difficulty dispensing substantially all of the liquid by the end of the infusion period. It is undesirable to have liquid remaining in the bladder.

Various materials are used for constructing conventional inflatable elastomeric bladders. For example, natural rubber is frequently used. Some construction requires several layers of material. The use of silicone in tube form to function as a pressurized liquid reservoir for infusion purposes is described in, for example, U.S. Pat. No. 4,909,790 which discloses an infusion device that uses tubular bladders mounted on mandrel supports with downstream restrictors to deliver uniform flow rates. Another example may be found in U.S. Pat. No. 7,704,230 which describes a pressurized fluid reservoir made from a silicone tube for an infusion system. Such references point to numerous possible combinations of silicones, structural dimensions, filling pressures, operating pressures, and fill volumes. However, the performance provided by the silicone tube disclosed in U.S. Pat. No. 7,704,230 has been found to be unacceptable for use at least because of the variability in flow rate and the pressure during the infusion period and the difficulty dispensing substantially all of the liquid by the end of the infusion period.

BRIEF SUMMARY OF THE INVENTION

The problems described above are addressed by the present invention which encompasses an improved elastomeric pump for an infusion assembly. The pump includes:

(a) a mandrel having a generally cylindrical body having a first end and an opposed second end, a length, a generally uniform outer diameter that corresponds to a first radius ($R_{mandrel}$), a central bore extending through the length, a first port positioned between the first end and second end and extending from the outer diameter to the bore to provide a fluid passageway, a fill port at about the first end in fluid communication with the bore, and exit port at about the second end in fluid communication with the bore; and (b) an inflatable tube disposed concentrically about the mandrel, the tube positioned between the first end and second end of the mandrel and covering the first port, the tube being sealingly secured on the mandrel near the respective ends of the tube and having an original inner diameter that corresponds to a second radius (r) so that it approximately matches the outer diameter of the mandrel ($R_{mandrel}$), a length (L) less than the length of the mandrel, a wall thickness (t) such that:

$$(0.4225 \times r) < t \leq (0.660 \times r).$$

According to an aspect of the invention, the inflatable tube further includes a volume ($v_{tube}$) of an elastomeric material:

$$v_{tube} = \pi L(2rt + t^2).$$

The elastomeric material is desirably an elastomeric silicone. The elastomeric silicone desirably has a Shore Hardness (durometer hardness) of about 25 A to about 35 A (as initially reported by the manufacturer) and has a Shore Hardness (durometer hardness) after processing into an inflatable tube of between about 30 A and about 40 A. More desirably, the elastomeric silicone has a Shore Hardness (durometer hardness) after processing into an inflatable tube of about 35 A to about 40 A. According to the present invention, the introduction of a volume of liquid ($v_{liquid}$) between the mandrel and the inflatable tube expands and pressurizes the tube such that the pump subsequently dispenses substantially all the volume of liquid through the first port upon contraction of the tube to substantially its original inner diameter. The volume of liquid ($v_{liquid}$) is determined according to the following equation:

$$(12.50 \times v_{tube}) \leq v_{liquid} \leq (22.16 \times v_{tube})$$

and it is introduced through the fill port at a fill pressure of greater than 0 and less than 35 psig.

The present invention also encompasses an elastomeric pump for an infusion assembly as generally described above wherein the pump dispenses substantially all the volume of liquid through the first port.

Generally speaking, the present invention relates to the discovery of certain relative ratios of tube wall thickness and liquid fill volumes that result in specific pressure ranges for the purpose of infusing 50-600 ml of liquid at relatively uniform flow rates until almost all the liquid is expelled. According to an aspect of the invention, the expansion of the tube to contain a given fill volume (e.g., 50-600 milliliters) may be readily accomplished by manual injection from a syringe device (filling pressure upstream of the tube is less than 35 psig). In another aspect of the invention, there is minimal residual volume of liquid in the tube after expelling substantially all of the liquid (i.e. less than 4 milliliters of liquid remaining in the inflatable tube). In another aspect of the invention, delivery of at least 60% of the fill volume of liquid is at a substantially uniform flow rate at pressures of 6.0-14.0 psig (as measured downstream of the expanded inflatable tube). In yet another aspect of the invention, the inflatable tube is a single monolithic or homogeneous tubular material. That is, the inflatable tube desirably lacks discrete layers and is a single extruded piece of tube. Desirably the inflatable tube is a single monolithic or homogenous silicone tube.

Other objects, advantages and applications of the present disclosure will be made clear by the following detailed description of a preferred embodiment of the disclosure and the accompanying drawings wherein reference numerals refer to like or equivalent structures.

DETAILED DESCRIPTION

Figure 1A:
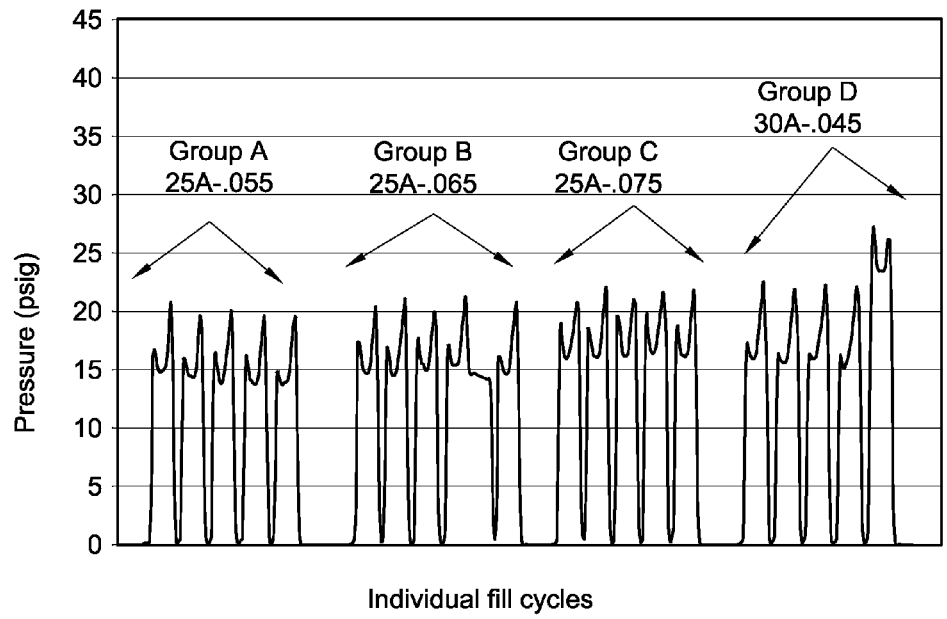
FIGS. 1A and 1B are illustrations of a graph of data and information from Crack Pressure and Fill Pressure testing of comparative examples of inflatable tubes.

Reference will now be made in detail to one or more embodiments, examples of which are illustrated in the drawings. It should be understood that features illustrated or described as part of one embodiment may be used with another embodiment to yield still a further embodiment.

The improved inflatable elastomeric pump for an infusion assembly may have the general configuration as described in U.S. Pat. No. 5,284,481 for "Collapsible Compact Infusion Apparatus" issued Feb. 8, 1994 to Soika et al., the entire contents of which are incorporated herein by reference. Deficiencies of the elastomeric pump portion of infusion pumps discussed at column 1 of that reference are addressed by the improved inflatable elastomeric pump as described herein.

Figure 9:
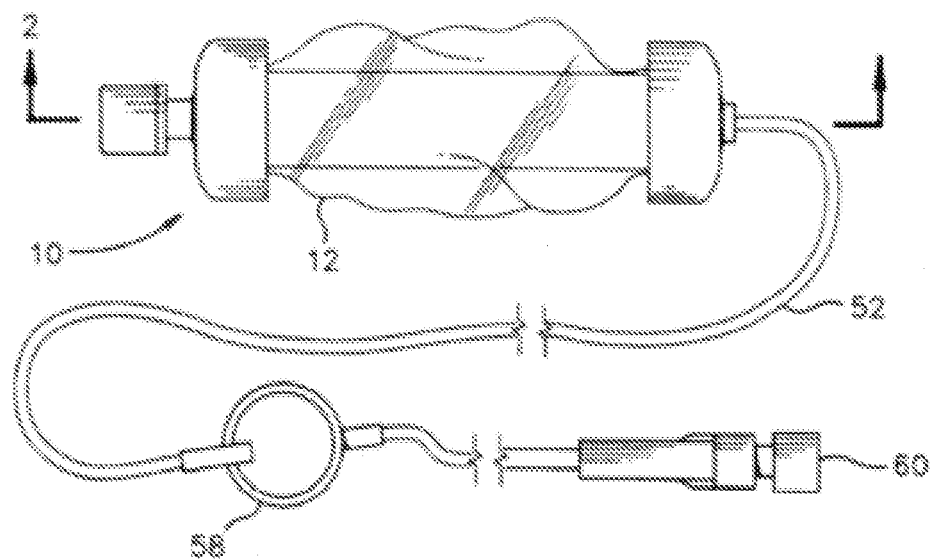
FIG. 9 is a top plan view of an exemplary inflatable elastomeric pump.
Figure 10:
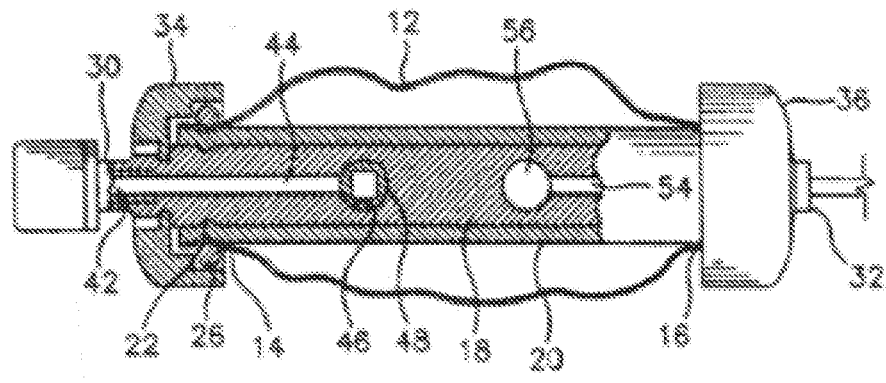
FIG. 10 is a view taken on line 2-2 of FIG. 9.

Referring to the drawings, and particularly to FIGS. 9 and 10, there is illustrated an exemplary embodiment of an infuser pump in accordance with the invention. The infuser pump, designated generally by the numeral 10, is collapsible and comprises an outer collapsible substantially non-stretchable housing or shell 12, protectively mounted over a combined reservoir and support assembly.

The collapsible housing 12 has a substantially spherical configuration for confining and guiding the inflatable reservoir or bladder into a concentric position around the central support member, and enabling it to expand naturally in a spherical configuration as will be described. The collapsible housing 12, as seen in FIG. 10, has coaxial openings defined by tubular sleeve extensions 14 and 16 through which the ends of a central support member 18 extends. An elastic membrane or bladder assembly 20 forming an inflatable reservoir, such as described in the aforementioned patents, is mounted on the cylindrical support member 18. The bladder assembly 20 may be a single sleeve or multiple sleeves, as set forth in the prior patents. This is preferably with an inner sleeve being a chemically inert sleeve, and the outer sleeve or sleeves being highly elastic.

The central cylindrical support member or mandrel 18 includes circular grooves only one of which, 22 is shown, at the ends thereof into which portions of the sleeve 20 and housing 12 are biased by means of a pair of 0-rings, only one of which, 26, is shown. The collapsible housing 12 is preferably a non-stretch blow molded housing of from five to ten mils in thickness and made of a material such as polyurethane, PVC film, and/or polyethylene and is transparent. This forms a simple inexpensive compact unit with a certain amount of protection for the elastic reservoir. Certain applications may require a tougher collapsible housing. In such cases, the housing should be transparent, UV stable, flexible and highly resistant to puncturing. The housing would be constructed of a material such as tough composites in a flexible form such as a fabric. Examples of such material are available under the trademark Kevlar.

The ends of the central support member 18 include reduced diameter extension 30 and 32, with bayonette type couplings for releasably coupling cup-shaped caps 34 and 36 which extend over and protectively cover the O-ring connections or clamping of the elastic bladder and collapsible housing to the support member. The member 32 has flat sides for receiving a similarly shaped opening in cap 36, with the cap 36 having inwardly extending flanges forming the flat sides which extend behind shoulders of the extension 32 for retaining the cap in place upon rotation of the cap ninety degrees relative to the member 32. This forms a quick and easy assembly construction for the protective cap.

The support member 18 has an inlet or fill port 42 on one end which communicates with a coaxial passage 44, and a transverse passage 46 in which is mounted a check valve 48. The cross bore 46 communicates with passage 44 and inlet port with the interior of the elastic bladder or sleeve 20 and thus the interior of the inflatable reservoir. The check valve is of a generally cylindrical outer shape, with a square bore extending from one end and closed at the other forming a cup-shaped structure. The check valve is constructed of an elastomer, such as silicone, and collapses inward to allow filling and erects to its normal configuration to prevent back flow. The square bore configuration of the bore insures that it returns to its normal configuration and does not remain collapsed.

An outlet port through end 32 communicates with a passage 54 that extends coaxially from the other end of the support member 18, and communicates with a cross bore or port 56 with the interior of the elastic bladder or reservoir 20. A tubing set, including a tube 52 having a filter 58 and a connector 60 at the end, provides a means for connecting and dispensing a fluid to a site, such as a vein of a patient.

The collapsible infuser apparatus of FIGS. 9 and 10 forms a compact and inexpensive disposable unit. It has a compact configuration, with a collapsed diameter no greater than the outer diameter of the caps 34 and 36.

Pressure conditions measured "upstream" or "downstream" of the invention will proportionally reflect conditions within the invention and specifically will reflect expansion and contraction states of the silicone tube. Upstream pressures characterize those pressures that act on the liquid as it is injected into the tube to expand the tube from an initial unexpanded state to the maximum expanded state. The maximum expanded state accommodates a Fill Volume. Because the liquid is injected from a syringe-type device through a one-way valve connector before it enters the tube, the pressure upstream of the one-way valve is dynamically measured while injection is occurring; hence these upstream pressures are greater than the pressures within the tube. (The syringe device and especially the valve connector can act as upstream flow restrictors and there typically is no allowance for equilibration of pressure conditions before and after the valve connector.) These upstream pressures move the liquid through the valve connector, then through one end of the mandrel and out the first port, and then against the inside surface of tube.

Figure 1B:
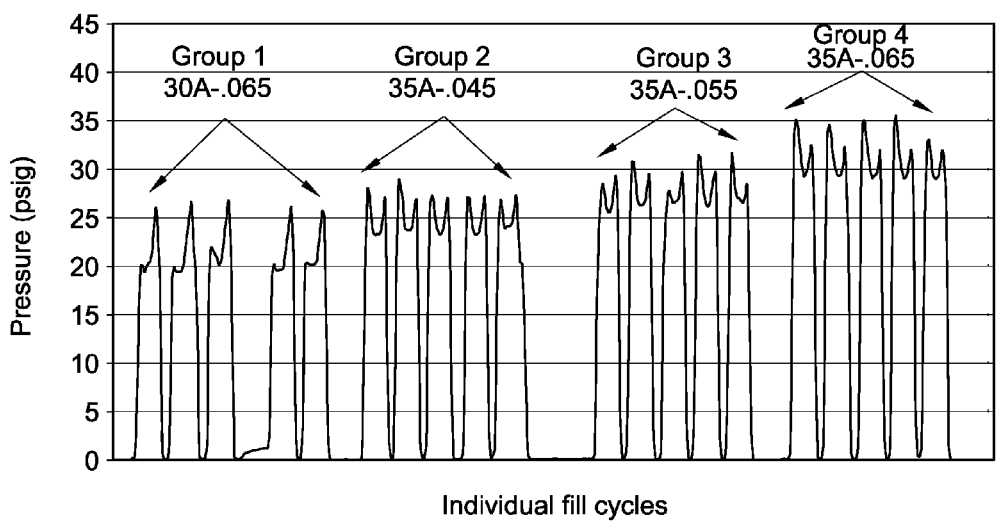

The measured upstream pressures ahead of the valve connector are termed Crack Pressures and Fill Pressures. The Crack Pressures indicate the forces that must be transmitted by the liquid to overcome the initial resistance to expansion of the inflatable tube. Fill Pressures indicate gradual expansion of the tube between the fixed ends attached to the mandrel; the expansion is in a general radial direction with respect to the center axis of the tube. The Fill Pressures initially decrease from the maximum Crack Pressure and then increase to a maximum when the Fill Volume is achieved. Typical measured upstream pressure data is shown in FIGS. 1A and 1B for multiple injection cycles into silicone tubes (one injection of 100 milliliters Fill Volume per tube). That is, FIGS. 1A and 1B are graphs of the measure pressure of liquid in the inflatable tube versus (y-axis) for an individual injection cycle in 5 individual tubes (x-axis) (each cycle, ~15 second in duration).

The tubes of FIGS. 1A & B all have 0.355" ID and 3.05" length but have different wall thickness and/or durometer hardness on mandrels of the same dimensions. As indicated on FIG. 1A: Groups A-C represent the injection of 100 milliliters (mls or ml) into 5 individual tubes made from an elastomeric silicone material having a measured durometer hardness of 25 A before processing into the tubes (i.e., a 25 A durometer hardness material) and with 0.055, 0.065, and 0.075 inch wall thickness respectively and Group D represents similar individual injections into tubes made from an elastomeric silicone material having a measured durometer hardness of 30 A before processing into the tubes (i.e., a 30 A durometer hardness material) with wall thickness of 0.045 inches. As indicated in FIG. 1B: Group 1 represents the injection of 100 ml into 5 individual tubes with 0.065 wall thickness and a 30 A durometer hardness material; Groups 2, 3, and 4 represent similar individual injections into tubes of 35 A durometer hardness material and respective wall thickness of 0.045, 0.055 and 0.065 inches. For each individual injection (cycle, ~15 second in duration) a maximum Crack Pressure is the left-most peak and a maximum Fill Pressure is the right-most peak.

The Groups of FIG. 1A and FIG. 1B illustrate the variations observed for Crack and Fill Pressures for silicone tubes in general (of the invention and not of the invention). Groups A-C (FIG. 1A) and Group 1 (FIG. 1B) exhibit maximum Crack Pressures that are less than the maximum Fill Pressures; Group 4 (FIG. 1B) exhibits the reverse; Groups D (FIG. 1A), Groups 2 and 3 (FIG. 1B) exhibit instances for such maximum pressures being greater than, less than, or equal to one another. The information depicted in FIGS. 1A and 1B suggests that for tubes of the same inner diameter (ID):

Silicone tubes of 30 A and less durometer hardness material exhibit maximum Crack Pressures that are less than the maximum Fill Pressures For silicone tubes of a given durometer hardness, the thicker the wall the greater the maximum Crack Pressure with respect to the maximum Fill Pressure More conclusive for tubes of a given ID are the following relationships among Fill Pressures, wall thickness, and durometer hardness:

At a given wall thickness, the greater the durometer hardness the greater the Fill Pressures At a given durometer hardness, the thicker the walls the greater the Fill Pressures Thus there are numerous combinations for durometer hardness and wall thickness that one can choose to achieve a specific maximum Fill Pressure.

Figure 2:
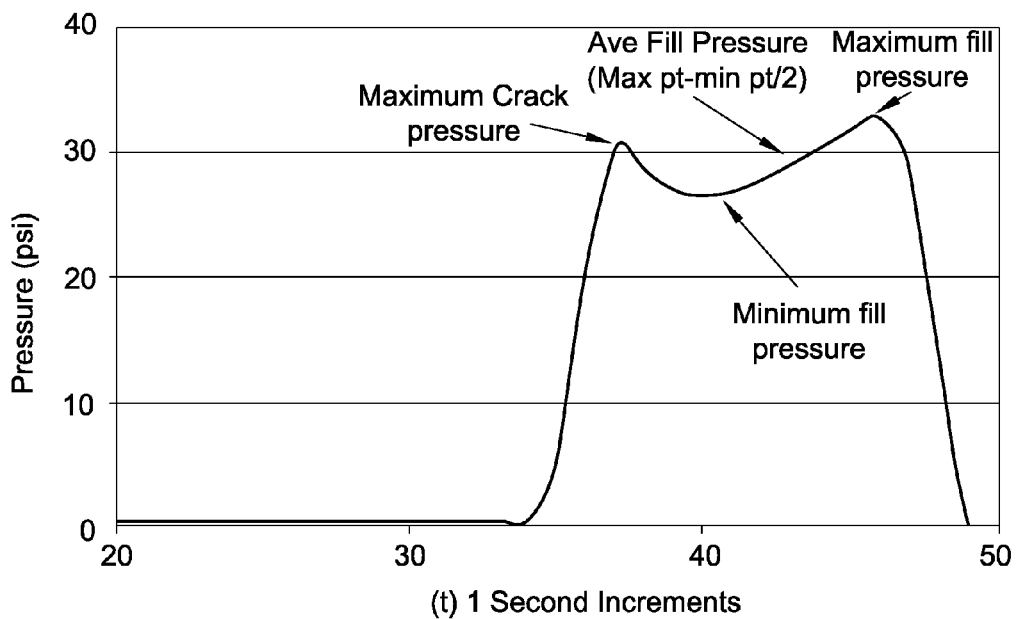
FIG. 2 is an illustration of a graph showing the minimum and maximum Fill Pressures that are used to calculate a single Average Fill Pressure for an exemplary improved inflatable elastomeric pump.

One method for recording Fill Pressures is to average the minimum and maximum Fill Pressures into a single Average Fill Pressure value for a given fill cycle. FIG. 2 illustrates such minimum and maximum data points for calculating an Average Fill Pressure (Ave Fill Pressure) for a mandrel supported silicone tube of the invention with the tube having a 0.10" wall thickness, an ID of 0.355 inches, and a length of 3.05 inches. In FIG. 2, the y-axis represents the pressure of liquid in the inflatable tube and the x-axis is time in seconds. The cycle is approximately 15 seconds in duration, starting at about 35 seconds and ending at about 50 seconds.

Table 1 gives such average values for the data represented in FIG. 1 and for additional groups T and E (, not shown in the FIG. 1 but with 5 individual fill cycles each) as; these Average Fill Pressure values correspond to the "Unsterilized As-Made" sample type values in Table 1. Also presented in Table 1 is data for other samples that are the same as the Unsterilized As-Made but after exposure to one of two types of sterilization: "Post-Gamma" values are for samples after their sterilization by exposure to gamma radiation; "Post-EtO" values are for samples after their sterilization by exposure to ethylene oxide. As the values of Table 1 indicate, ethylene oxide sterilization has negligible effect while gamma radiation increases the Crack and Fill Pressures by ~6 to ~16%. Such impact due to sterilization conditions is also observed for other silicone tubes of 30 A durometer hardness material with walls up to 0.180 inch thickness, and presumedly greater.

TABLE 1

| | Average Fill Pressure (PSIG) Group | | | | | | | | | |
|---|---|---|---|---|---|---|---|---|---|---|
| | T | A | B | C | D | E | 1 | 2 | 3 | 4 |
| | Durometer - Wall thickness | | | | | | | | | |
| Sample Type: | 25A-.045 | 25A-.055 | 25A-.065 | 25A-.075 | 30A-.045 | 30A-.055 | 30A-.065 | 35A-.045 | 35A-.055 | 35A-.065 |
| Unsterilized As-Made | 15 | 17 | 17.5 | 19 | 19 | 21 | 23 | 25 | 27 | 30 |
| Post-Gamma | 16 | 16 | 20 | 22 | 21 | 24 | 25 | 28 | 30 | 34 |
| Post-EtO | 15 | 17 | 17 | 20 | 20 | 21 | 24 | 25 | 28 | 31 |

FIG. 2 shows that both the maximum Crack and Fill Pressures are less than 35 psig; this criteria, regardless of time duration for the fill cycle, is a desirable characteristic of the invention.

While Crack and Fill Pressures reflect the pressure conditions that act on the silicone tubes, Operating Pressures directly provide information about the actual pressure conditions on the tubes. The Operating Pressures are measured downstream of the mandrel and silicone tube invention and have no intervening blockage in the liquid flow path from the silicone tube to the pressure sensor. Thus the pressure acting on the silicone tube is transmitted hydrostatically and continuously downstream of the invention. Because the downstream conduits are generally designed to delivery approximate flow rates of 1-4 ml/hour, pressure conditions against the silicone tube equilibrate relatively quickly with pressure conditions downstream of the mandrel and silicone tube assembly. When the pressure sensor is inserted into direct communication with the liquid in the conduit (e.g. tubing) within 2 feet of the first port the measured pressures via the sensor are essentially those acting on the silicone tube; thus such Operating Pressures are portrayals of the actual pressures on the silicone tube.

Figure 3:
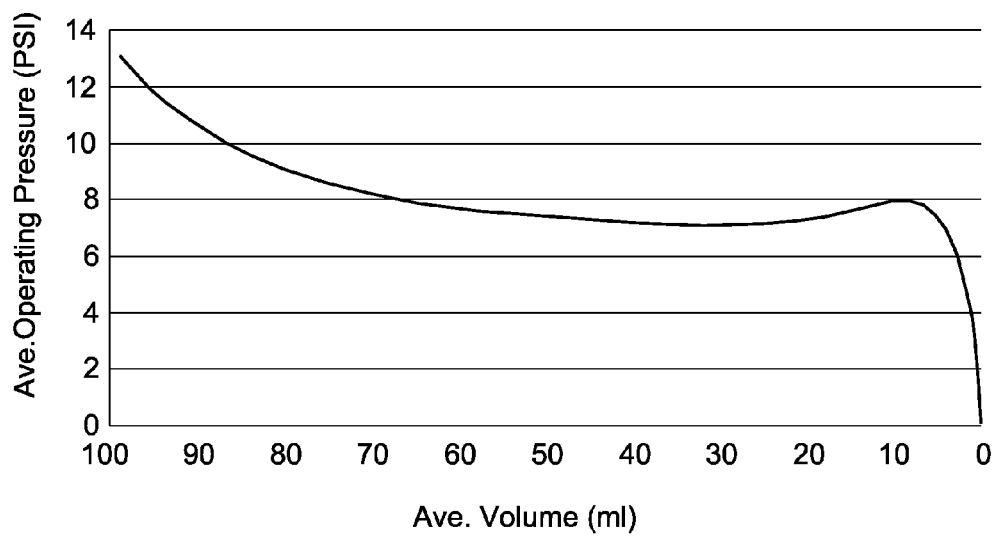
FIG. 3 is an illustration of a graph showing an exemplary depressurization curve (profile) for averaged operating pressures on the y-axis at averaged volumes on the x-axis for exemplary elastomeric pumps of the invention.

Silicone tubes of interest for the invention share a common characteristic "depressurization" profile as liquid, initially at a Fill Volume, is squeezed out of the silicone tube and delivered downstream over time. FIG. 3 provides an illustrative example of the characteristic depressurization curve; the example is representative of the dimensions of Tube 1 per Table 2 and of a silicone with a durometer hardness of 30 A. In FIG. 3, the y-axis is average operating pressure of liquid in the inflatable tube and the x-axis is volume of liquid in the tube.

Additional exemplary dimensions for silicone tubes of the invention are given in Table 2. Each of the tubes have mandrels that support the tube in the absence of contained liquid; the respective mandrel (for Tubes 1, 2, 3, 4) has an OD sized to match the ID of the tube and a length greater than the tube.

TABLE 2

| Tube Dimensions, inches | Silicone Tube | | | |
| --- | --- | --- | --- | --- |
|  | 1 | 2 | 3 | 4 |
| ID, inch | 0.355 | 0.6 | 0.6 | 0.6 |
| OD, inch | 0.555 | 0.88 | 0.88 | 0.96 |
| Wall, inch | 0.1 | 0.14 | 0.14 | 0.18 |
| Length, inch | 3.05 | 3.75 | 4.75 | 4.75 |
| Tube Volume, in$^3$ | 0.43597 | 1.22051 | 1.54598 | 1.65405 |
| Fill Volume, ml (in$^3$) | 100 (6.1024) | 250 (15.256) | 400 (24.409) | 600 (36.6140) |

Silicones with a durometer hardness (Shore hardness) of 35 A or less are suitable for forming the tube. Such silicones in the dimensions represented by Tubes 1-4 allow for allow expansion of the tube to contain liquids up to the indicated Fill Volumes. Appropriate selection of silicones are ones that: form inflatable tubes; result in any maximum pressures that are greater than 12 psig but less than 35 psig when inflated with a predetermined Fill Volume of liquid as measured a short distance downstream of the first port; and provide sufficent constricting forces to expel almost all the Fill Volume liquid. Exemplary silicones are: NUSIL 4020 (also called MED-4020) with a Shore hardness of 25 A (as reported by the manufacturer); NUSIL 4025 (also called MED-4025) with a Shore hardness of 30 A (as reported by the manufacturer); NUSIL 4030 (also called MED-4035) with a Shore hardness of 35 A (as reported by the manufacturer). NUSIL 4025 is a preferred silicone. The durometer hardness of the silicone that is used to make the tubes is a material parameter of the invention. Values for the durometer hardness are measured and given per the Shore A scale. The exemplary silicone polymers sold under the designation NUSIL MED-4020, MED-4025 and MED-4035, as well as other polymers (e.g., MED-4050, MED-4065) are available from NuSil Technology, LLC of Carpinteria, Calif., USA.

The Shore Hardness testing of plastics is most commonly measured by the Shore (Durometer) test using either the Shore A or Shore D scale. The Shore A scale is used for "softer" rubbers while the Shore D scale is used for "harder" ones. The Shore A Hardness is the relative hardness of materials such as rubber or soft plastics and can be determined with an apparatus known as a Durometer and is sometimes also referred to as Durometer Hardness (or durometer hardness).

The hardness value is determined by the penetration of the Durometer indenter foot into the sample. If the indenter completely penetrates the sample, a reading of 0 is obtained, and if no penetration occurs, a reading of 100 results. The reading is dimensionless. Because of the resilience of rubbers and plastics, the hardness reading may change over time so the indentation time is sometimes reported along with the hardness number. The durometer hardness values measured for the tubes presented in connection with this invention are determined per ASTM D2240 procedures and use a time interval of approximately 1 second between initial indentor travel cessation and the recording of the indicated reading (as considered standard). The analogous ISO test method to this ASTM test number is ISO 868. The given values for the material durometer hardness values are vendor provided.

It is noted that processing of the silicone into an inflatable tube and curing the tube may have an impact on the Shore Hardness. Sterilization of the tube and inflation/deflation or mechanical working of the material for at least one cycle may also have an impact on the Shore Hardness. Table 3 reports the Shore A Hardness measured for a series of inflatable tubes corresponding to Inflatable Tube #3 from Table 2 (Inside Diameter=0.6 inch, Outside Diameter 0.88 inch, Wall Thickness 0.14 inch, design volume 400 milliliters). These tubes were made by extruding NUSIL 4025 (Shore hardness of 30 A as reported by the manufacturer—also referred to as Shore A hardness of 30). Three (3) separate tubes were tested. The average results and corresponding standard deviations in Table 3 are for the extruded & cured tube; tube sterilized utilizing a conventional Ethylene Oxide (EO) sterilization cycle; and sterilized tube loaded with sterile water and allowed to deflate over a period of approximately 279 hours (i.e., cycled). The results are based on six (6) measurements per tube.

TABLE 3

| SAMPLE | SHORE A HARDNESS Average: n = 6 | Standard Deviation |
| --- | --- | --- |
| Extruded & Cured | 37.00 | 1.14 |
| EO Sterilized | 36.83 | 2.70 |
| EO Sterilized & Cycled | 36.75 | 1.37 |

As can be seen from Table 3, extruding the Nusil 4025 into inflatable tubes and curing the tubes with heat increases the Shore A hardness from a nominal value of 30 (as reported by the manufacturer) for the unprocessed material to a value of about 37 for the tube. Sterilization with ethylene oxide and recoverable stretching do not appear to produce a meaningful change to the Shore A hardness.

A structural parameter of the invention is the wall thickness, t, of the inflatable tube. An exemplary range of wall thicknesses for silicone tubes made from NUSIL 4025 are greater than 0.075 inches up to 0.180 inches. Another structural parameter is the inner diameter, ID, of the tube and exemplary ranges are 0.355 inches to 0.600 inches. Another parameter is the length, L, of the tube. The Tube Volume (equivalently TubeVol and $v_{tube}$) is derived from these parameters according to conventionally accepted mathematical relationships. Also from the t, ID, L, and TubeVol values are certain ratios that can characterize the invention.

Appropriate combinations of the structural and material parameters yield tubes of the invention that accommodate Fill Volumes from 50-600 ml of liquid.

each profile have similar pressure values. As shown subsequently, the differences in the maximum Operating Pressures can be explained via ratios that are based on certain structural parameters.

Figure 4:
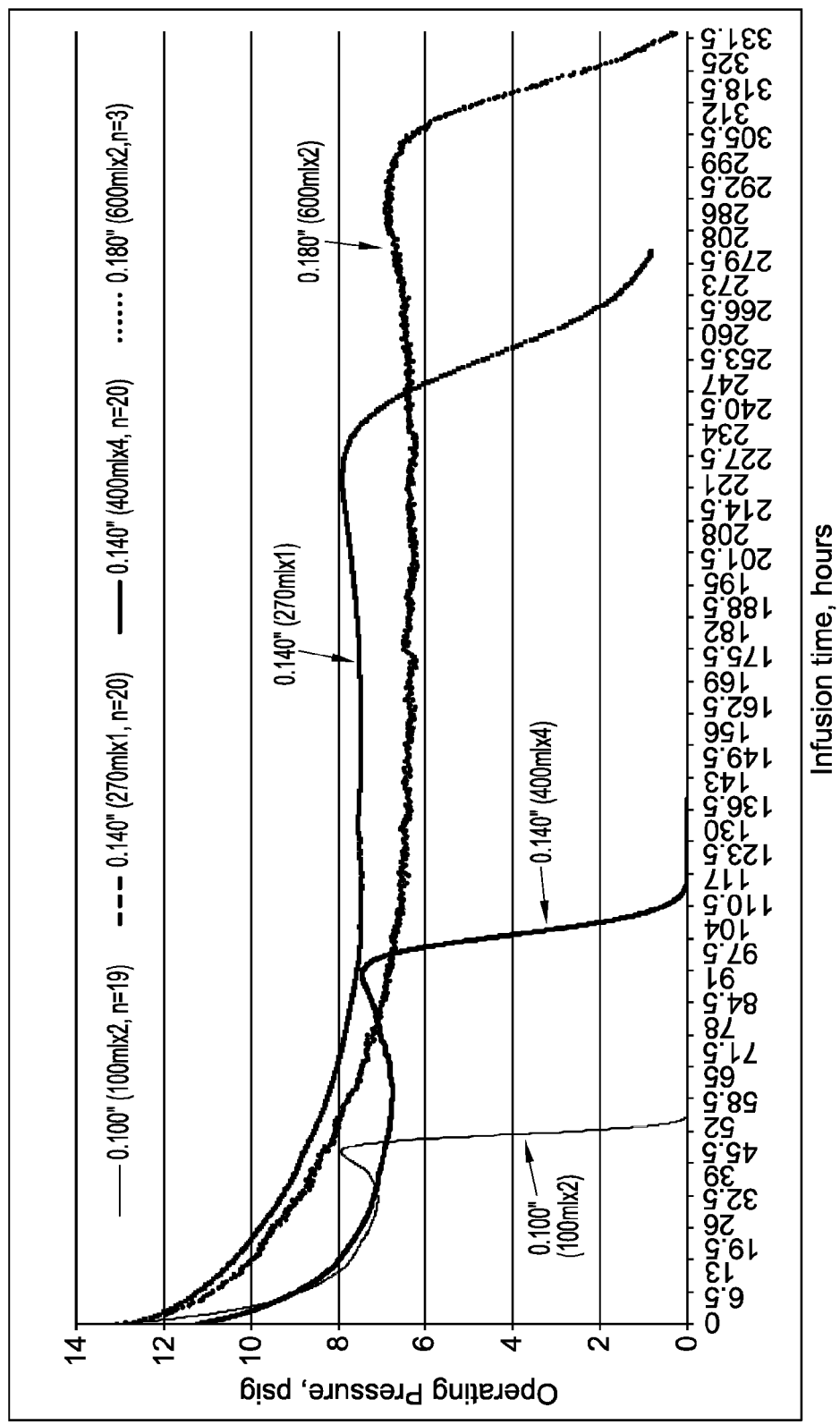
FIG. 4 is an illustration of a graph showing averaged Operating Pressure profiles for exemplary expanded tubes of exemplary elastomeric pumps that track their depressurization from their Fill Volumes with respect to time (Infusion Time).

FIG. 4 also indicates that almost all of the Fill Volume liquid is expelled at the completion of depressurization. This is an important feature of the invention. Desirably, none of the tubes of the invention retain more than just a few milliliters of liquid upon complete depressurization. For example, the tubes of the present invention retain less than about 10 mls of liquid upon complete depressurization. As another example, the tubes of the present invention retain less than about 5 mls of liquid upon complete depressurization. As yet another example, the tubes of the present invention retain less than about 4 mls of liquid upon complete depressurization. As still another example, the tubes of the present invention retain less than about 2.5 mls of liquid upon complete depressurization.

TABLE 4

| Ex. | Structural Parameters that correspond to Table 2 Silicone Tube | Description per FIG. 4 | Design Flow rate, ml/hr | Fill Volume, ml | Operating Pressure, psig | ~0 Infusion time, hrs | Calculated Expel Time, hr |
|---|---|---|---|---|---|---|---|
| 1 | 1 | 0.100" (100 ml × 2, n = 19) | 2 | 100 | 13.14 | 0 | 50 |
| 2 | 2 | 140" (270 ml × 1, n = 20) | 1 | 270 | 12.58 | 0.5 | 270 |
| 3 | 3 | 140" (400 ml × 4, n = 20) | 4 | 400 | 11.24 | 0.083 | 100 |
| 4 | 4 | 180" (600 ml × 2, n = 3) | 2 | 600 | 13.09 | 0 | 300 |

FIG. 4 shows averaged Operating Pressure profiles for expanded tubes that track their depressurization of liquid expelled from the expanded tube beginning from their Fill Volumes with respect to time (Infusion Time) reported in hours. The tubes used in making FIG. 4 are examples of the invention, have the structural parameters of Table 2, and are made from NUSIL 4025 silicone which has a material parameter of 30 A durometer hardness. Table 4 identifies these examples as Examples 1-4 and their respective connection to Table 2. Table 4 also specifies the Operating Pressure at ~0 Infusion Time, which is essentially the equilibrated pressure that acts against the tube wall while containing all the Fill Volume. Additional information in Table 4 provides the Design Flow rates that indicate the degree of downstream restrictions that are intentionally made to modulate the flow rate and specifies the number of individual samples for the examples that were used to obtain the averaged Operating Pressure profiles.

Figure 5:
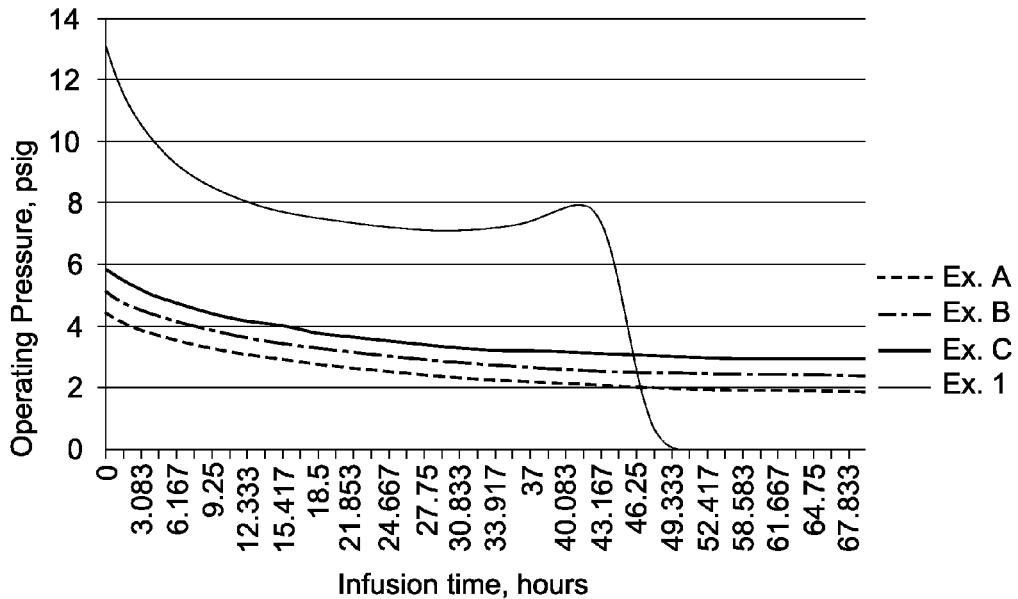
FIG. 5 is an illustration of a graph showing Operating Pressure versus infusion time as measured downstream from the inflatable tube and mandrel for four different sample sets of silicone tubes.

Each profile of FIG. 4 displays the depressurization characteristics of FIG. 3: a maximum Operating Pressure at 0 Infusion time, a second peak towards the completion of depressurization, and a generalized plateau between the maximum Operating and second peak pressures. The pressure values for Ex. 1 are similar to those for the tube of FIG. 3 (Tube 1) as expected since they have structural and material parameters in common. FIG. 4 shows them with pressures with respect to time while FIG. 3 shows them with respect to expelled volume (volume in the tube and infusion time are interrelated). It is noteworthy that the second peaks and plateaus of For purposes of characterizing tubes that are not representative of the invention, it has been found that tubes made from NUSIL 4025 (material durometer hardness=30 A) with wall thickness of 0.075 or less lack sufficent constricting forces in the expanded tube to expel almost all of the Fill Volume at the desired Operating Pressures. The importance of having sufficent constricting force to expel the Fill Volume liquid is shown in FIG. 5. More particularly, FIG. 5 is a graph of Operating Pressure of liquid expelled from the tube (that is measured downstream from the silicone tube and support mandrel and before flow restrictors) for four different sample sets of silicone tubes versus infusion time (reported in hours). All the tubes were made from NUSIL 4025 (Shore hardness 30 A) with a length of 3.05 inches and an ID of 0.355 inches and were filled with a Fill Volume liquid of 100 ml.

The top curve of FIG. 5 represents Ex. 1, a tube with 0.100" thick wall and indicates acceptable pressure behavior with respect to the invention; the next highest curve represents Ex. C, a tube with 0.075" thick wall; the following curve represents Ex. B, a tube with 0.065" thick wall; and the lowest curve represents Ex. A, a tube with 0.055" thick wall. After 50 hours, only the tube with 0.100" thick wall expelled all of the Fill Volume liquid; the other tubes had insufficient constricting forces to overcome the downstream restrictions that dramatically slowed expulsion of the 100 ml Fill Volume from those tubes. FIG. 5 also provides a comparison of the maximum Operating Pressures that expand the tube walls away from the mandrel when the tubes contain all 100 ml of the Fill Volume liquid; these pressures are the "Y" intercepts of the curves at 0 Infusion time. (At 0 Infusion time, when none of the Fill Volume has been expelled, the Operating Pressure essentially equals the expanding pressure that provides the force to counter the constricting forces that are inherent in the tube.) These expanding pressures for 100 ml Fill Volume liquid are given in Table 5.

TABLE 5

0.355" ID x 3.05" length tubes from NUSIL 4025 silicone (Shore hardness of 30A - as reported by manufacturer) supported on matching mandrels

| | Example | | | |
|---|---|---|---|---|
| | Ex. A | Ex. B | Ex. C | Ex. 1 |
| Tube Wall, inch | 0.055 | 0.065 | 0.075 | 0.100 |
| Expanding pressure, psig (at 0 Infusion time) | 4.434 | 5.0875 | 5.874 | 13.138 |

To further establish the direct connection between Operating Pressures and pressures acting against the tubes the following 'static' experiment was conducted. The pressures at a very short distance downstream of the first port were recorded as selected mandrel-supported silicone tubes, suitable for the invention, were inflated to and deflated from Fill Volumes in 25 ml increments. The selected tubes are identified as Ex. 11, 21, 31, and 41 and are described with respect to structural parameters in Table 6. These tubes were made from NUSIL 4025, thus their material parameter was a durometer hardness of 30 A. That is, the tubes were made from a material having a durometer hardness of 30 A prior to processing into the tubes. Table 6 also reproduces the recorded pressures (pressure data points) for each Ex. 11, 21, 31, and 41 with respective Fill Volumes of 100, 250, 400, and 600 milliliters as obtained via the following 'Inflation/Deflation Curves' Procedure. These pressures were graphed in FIG. 6 with respect to volume to give an inflation curve towards each respective Fill Volume and a deflation curve away from the Fill Volume. (The pressure data points for injecting are shown as solid markers; those of dispensing are unfilled markers.)

Inflation/Deflation Curves Procedure for Ex. 11, 21, 31, and 41 (the Static Experiment):

1. Obtain a new mandrel and silicone tube assembly with attached downstream conduit 2. Cut the downstream conduit approximately 5" from its connection end to the mandrel and attach male Luer with two connection ports, one with a valve mechanism that is closed.

3. Connect the pressure transducer to the connection port without the valve mechanism and prime the line with saline before connection.

4. Using a syringe, inject 25 ml of saline for each pressure data point through the valve mechanism when opened.

5. Measure pressure one minute after each injection.

6. Repeat until Fill Volume is obtained.

7. Measure pressure as the silicone tube is depressurized (emptied) dispense 25 ml at a time by opening the valve mechanism. Measure pressure one minute after 25 ml is dispensed until all of the Fill Volume is removed.

TABLE 6

Pressure, PSI for: Reservoir Tube

| | Ex. 11 | | Ex. 21 | | Ex. 31 | | Ex. 41 | |
|---|---|---|---|---|---|---|---|---|
| | Tube Exterior Dimensions | | | | | | | |
| | 0.555" OD x 3.05" L | | 0.880" OD x 3.75" L | | 0.880" OD x 4.25" L | | 0.960" OD x 4.25" L | |
| | Wall thickness | | | | | | | |
| | 0.10" | | 0.14" | | 0.14" | | 0.18" | |
| Vol, ml | to Fill Vol | from Fill Vol | to Fill Vol | from Fill Vol | to Fill Vol | from Fill Vol | to Fill Vol | from Fill Vol |
| 0 | 0 | 0 | 0 | 0 | 0 | 0 | 0 | 0 |
| 25 | 13.39 | 7.99 | 14.71 | 8.29 | 14.43 | 7.36 | 18.53 | 7.78 |
| 50 | 14.46 | 8.21 | 14.5 | 7.93 | 14.41 | 7.5 | 18.83 | 8.65 |
| 75 | 16.31 | 10.17 | 14.09 | 7.81 | 13.32 | 7.07 | 17.74 | 8.37 |
| 100 | 18.11 | 18.11 | 14.1 | 7.73 | 13 | 6.95 | 16.95 | 7.92 |
| 125 | | | 14.23 | 7.98 | 12.91 | 6.95 | 16.58 | 7.68 |
| 150 | | | 14.49 | 8.37 | 12.86 | 6.9 | 16.4 | 7.49 |
| 175 | | | 14.81 | 8.75 | 12.36 | 6.96 | 16.28 | 7.6 |
| 200 | | | 15.12 | 9.72 | 12.67 | 7.01 | 16.25 | 7.61 |
| 225 | | | 15.35 | 11.1 | 12.87 | 7.31 | 16.31 | 7.69 |
| 250 | | | 15.59 | 15.59 | 13.1 | 7.73 | 16.41 | 7.61 |
| 275 | | | | | 13.32 | 8.08 | 16.5 | 7.79 |
| 300 | | | | | 13.53 | 8.64 | 16.53 | 8 |
| 325 | | | | | 13.77 | 9.33 | 16.42 | 8.18 |
| 350 | | | | | 14.01 | 9.98 | 16.39 | 8.1 |
| 375 | | | | | 14.27 | 11.16 | 16.43 | 8.42 |
| 400 | | | | | 14.54 | 14.54 | 16.54 | 8.69 |
| 425 | | | | | | | 16.66 | 9.15 |
| 450 | | | | | | | 16.81 | 9.43 |
| 475 | | | | | | | 17.01 | 10.28 |
| 500 | | | | | | | 17.24 | 10.84 |
| 525 | | | | | | | 17.5 | 11.81 |
| 550 | | | | | | | 17.75 | 12.65 |
| 575 | | | | | | | 18.01 | 13.97 |
| 600 | | | | | | | 18.3 | 18.3 |

Figure 6:
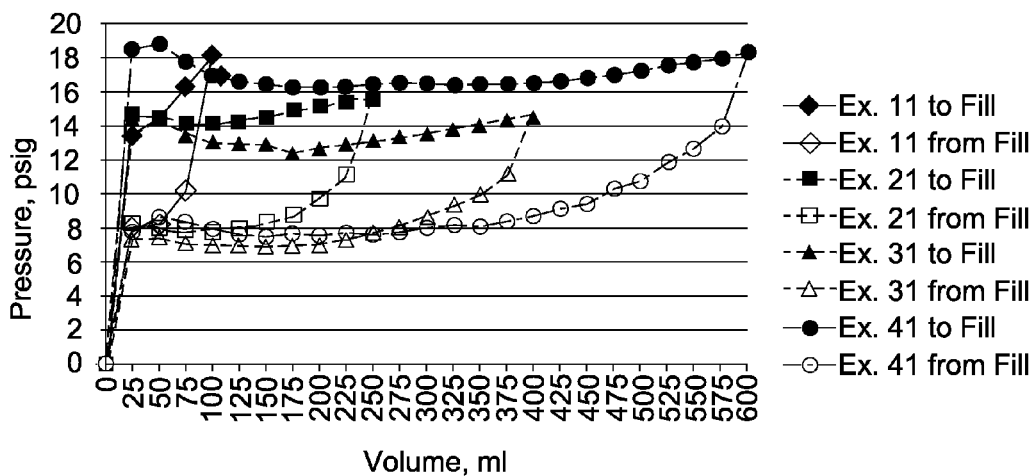
FIG. 6 is an illustration of a graph showing the pressure on the y-axis and the volume on the x-axis for respective pressurization and depressurization cycles for exemplary improved inflatable elastomeric pumps.

The inflation curves of FIG. 6 share characteristics of the Crack and Fill Pressures previously described and the deflation curves closely mirror the Operating Pressures for tubes of similar structural and material parameters and relatively similar Fill Volumes. Table 7 compares maximum, second peak and general plateau pressures as shown in FIG. 6 per Table 6 with maximum, second peak, and general plateau Operating Pressures as given in previous Tables and Figures.

The magnitudes of the pressures at the Fill Volumes of FIG. 6 also indicate a relationship between pressure and actual wall thickness. Ex. 11 with the thinnest initial wall and shortest for length, thus it has the smallest Tube Volume (per Table 8, equivalent to dimensions of Tube 1 per Table 2), has a pressure at its Fill Volume (100 ml) that is comparable to that for Ex. 41 (at 600 ml Fill Volume), which has the thickest initial wall and longest length, hence the greatest Tube Volume (per Table 8, equivalent to dimensions of Tube 4 per Table 2). Ex. 21 and Ex. 31 have lower pressures at their Fill Volumes.

One explanation for the magnitude differences in pressures at respective Fill Volumes is that: Ex. 11 and Ex. 41 should have comparably thinner actual walls at their Fill Volumes compared to Ex. 21 and Ex. 31 and therefore exert the greater constricting forces per unit surface area at these Fill Volume; Ex. 21 should have the next thinner actual wall at its Fill Volume and thus the next greater constricting force per unit area; Ex. 31 should have an actual wall thickness at its Fill Volume that is greater than that of Ex. 21 and therefore has less constricting force per unit surface area. In other words Ex. 11 and Ex. 41 are expanded (stretched) more towards their limit of plastic deformation (yield point, past which the tube will not quickly return to its original dimensions before filling). Ex. 21 and 31 should be respectively thicker and thus should allow for more expansion before reaching the actual thinness of Ex. 11 at its Fill Volume. The Operating Pressures of Ex. 1-4 per Table 7 show similar magnitude differences that are consistent with the offered explanation: the maximum pressure of Ex. 1 (like Ex. 11) is comparable to Ex. 4 (like Ex. 41) while the maximum pressures for Ex. 2 (like Ex. 21) and Ex. 3 (like Ex. 31) are less.

The offered explanation is further supported when the shape of each tube at its Fill Volume is assumed to be a sphere and tube is assumed to form a shell around the sphere. Given the accepted volume-to-radius relationship for a sphere, the above assumptions, and the appropriate values of Table 8, the shell thicknesses at each Fill Volume calculate as: 0.0264" for Ex. 11, 0.0306" for Ex. 41; 0.0399" for Ex. 21; 0.0372" for Ex. 31.

Table 7 also gives maximum pressure values (all Operating Pressures) for examples Ex. A, B, and C, which are lower than Ex. 1, and thus in contradiction to the preceding explanation. This contradiction can be explained if the initial Crack and Fill Pressures for Ex. A, B, and C tubes produced stretching forces that closely approached or exceeded the limit of plastic deformation so that these tubes will not recover their initial dimensions. The lack of respective second peaks in pressure per FIG. 5 indicates this is the case.

Table 7 allows comparisons of the maximum pressures at Fill Volumes (Fill) for tubes that are essentially the same: values for Ex. 11 to those of Ex. 1; those of Ex. 21 to those of Ex. 2; etc. The difference in the maximum pressures at Fill can be explained as stress relaxation phenomena common to elastomeric materials. The measured pressures at Fill for Ex. 11-Ex. 41 were all made 1 minute after the Fill volume was attained. The maximum pressures for Ex. 1-4 are the Operating Pressures at 0 infusion time, which implies these examples have been containing the same respective Fill Volumes as for Ex. 11-Ex. 41 for sufficiently long enough periods of time to allow some of the molecular entanglements that are initially present when the tubes are inflated to rearrange and dissipate some of the constricting energy. Indeed, should the maximum pressure for Ex. 11 have been held for a time longer than that given per the procedure, it is conceivable that the maximum pressure value for Ex. 11 will decay to the lower maximum pressure value for Ex. 1. In other words, the maximum pressures at Fill per the Inflation/Deflation Curves procedure should decay to the equilibrium pressures as represented by the Operating pressures at) infusion time.

TABLE 7

| Tube | Source | Wall × Length, inch | Maximum at Fill | Second Peak | Plateau |
|---|---|---|---|---|---|
| Ex. 11 | Table 6 | 0.010 × 3.05 | 18.11 | 7.99 | 7.99-8.21 |
| Ex. 1 | FIG. 4 data; FIG. 3 | | 13.14 | 7.94 | 7.94-9.01 |
| Ex. 21 | Table 6 | 0.140 × 3.75 | 15.59 | 8.29 | 8.29-9.72 |

TABLE 7-continued

| Tube | Source | Wall × Length, inch | Maximum at Fill | Second Peak | Plateau |
|---|---|---|---|---|---|
| Ex. 2 | FIG. 4 Data | | 12.56 | 7.50 | 7.50-8.35 |
| Ex. 31 | Table 6 | 0.140 × 4.75 | 14.54 | 7.50 | 7.50-9.33 |
| Ex. 3 | FIG. 4 data | | 11.24 | 7.46 | 7.46-8.50 |
| Ex. 41 | Table 6 | | 18.3 | 8.65 | 8.65-9.43 |
| Ex. 4 | FIG. 4 data | 0.180 × 4.75 | 13.09 | 6.81 | 6.81-7.02 |
| Ex. A | Table 2; FIG. 5 | 0.055 × 3.05 | 4.43 | — | 2.80-3.00 |
| Ex. B | Table 2; FIG. 5 | 0.065 × 3.05 | 5.09 | — | 2.90-3.50 |
| Ex. C | Table 2; FIG. 5 | 0.075 × 3.05 | 5.87 | — | 3.80-4.20 |

When ratios based on structural parameters for the tubes of Table 6 are compared in light of their pressure values, these ratios point to ranges that characterize the suitability for use in the invention. Table 8 lists structural parameters and various ratios based on them. Of primary relevance for defining dimensions for tubes that may be suitable candidates for use in the invention are the ratios of wall thickness t to tube inner radius r or the outer radius as shown in items j) and k) respectively. Since these ratios are expressions of the same structural parameters, item j), the ratio of t to the inner tube radius r, will be used to identify limitations. Of secondary relevance is the ratio for the Fill Volume to the Tube Volume, as shown in item l). Given that tubes of Ex. 1-4 and Ex. 11-41 (all from 30 A durometer hardness material) exhibit preferred pressure behavior up to their respective Fill Volumes, their ratio values per item j) and item l) are within the range of acceptability for the invention. Since Ex. C exhibits unacceptable pressure behavior at its indicated Fill Volume, the value of the j) ratio lies outside the lower limit of acceptability. The value of the item j) ratio for Ex. 4 & Ex. 41 is determined to be within the acceptable range per its pressure behavior up to its Fill Volume and sets an upper limit in light of the value for the ratio of item l) versus those for Ex. A and Ex. B, which have unacceptable pressure behaviors for their Fill Volumes. In other words, acceptable structural parameters for tubes suitable for the invention are defined by item j) ratios from greater than 0.42254 to 0.6.

Figure 7:
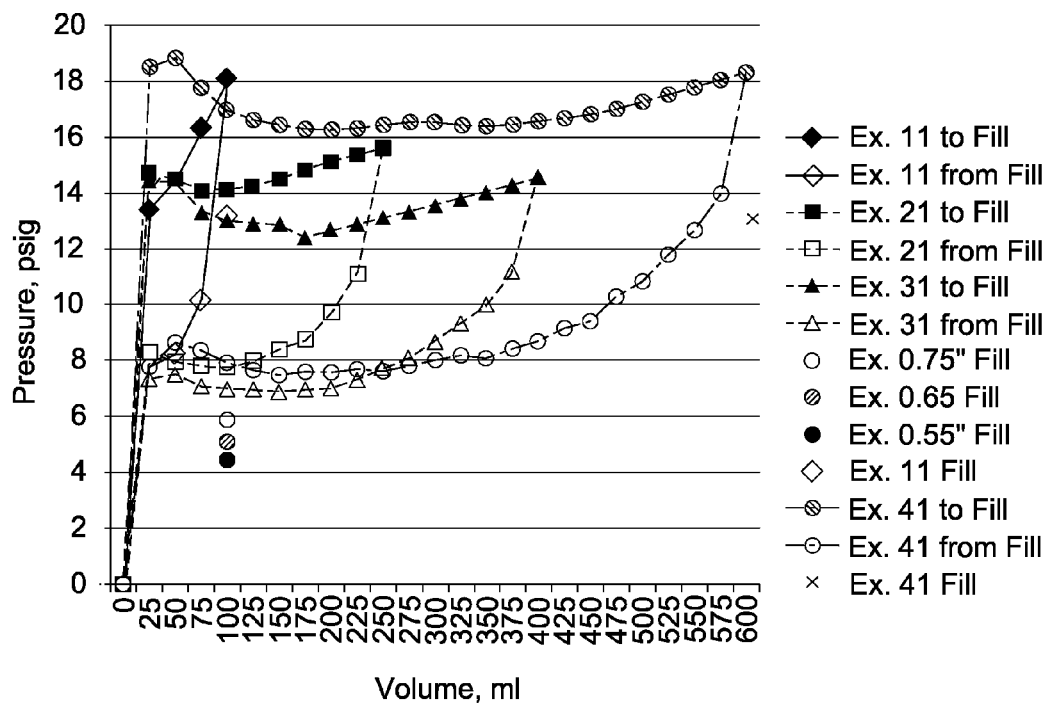
FIG. 7 is an illustration of the graph of FIG. 6 but also including additional information from Table 6 for Examples A-C as well as Example 4.
Figure 8:
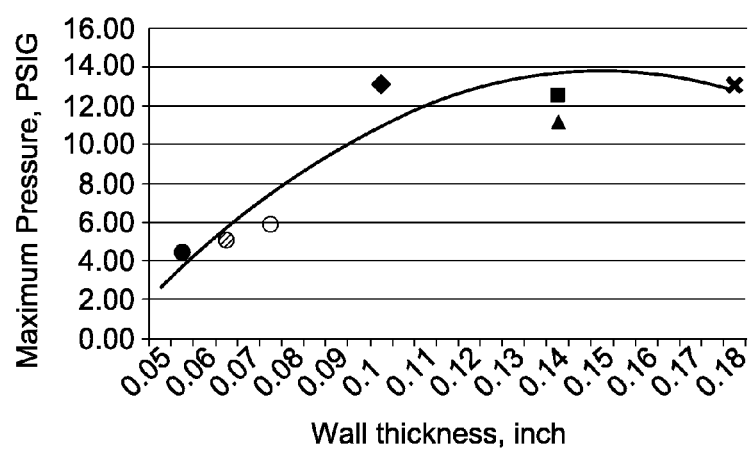
FIG. 8 is an illustration of a graph showing a pressure curve resulting from the Fill values of FIG. 7 with respect to their corresponding wall thickness.

A graphic depiction of such an acceptable range is illustrated by FIG. 8 which is derived from Fill values of FIG. 7 that are based on Table 7 data points for maximum at Fill values that correspond to Operating pressures at 0 infusion time. FIG. 7 shows the same information as FIG. 6 but includes the maximum pressures per Table 7 for Ex. A-C (unacceptable for the invention) and Ex. 1-4 (acceptable for the invention). FIG. 8 plots the maximum pressures per Table 7 for Ex. A-C and Ex. 1-4 with respect to their corresponding wall thickness; clearly a lower bound of acceptability for tubes with ID values of 0.355 inches exists for wall thickness between 0.075 and 0.100 inches and an upper bound seemingly exists for tubes of ID values of 0.600 inches and a wall thickness of or near 0.180 inches.

TABLE 8

| | item | Ex. A | Ex. B | Ex. C | Ex. 1 & Ex. 11 | Ex. 2 & Ex. 21 | Ex. 3 & Ex. 31 | Ex. 4 & Ex. 41 |
|---|---|---|---|---|---|---|---|---|
| a) | ID, in | 0.355 | 0.355 | 0.355 | 0.355 | 0.6 | 0.6 | 0.6 |
| b) | OD, in | 0.465 | 0.485 | 0.505 | 0.555 | 0.88 | 0.88 | 0.96 |

TABLE 8-continued

|  | item | Ex. A | Ex. B | Ex. C | Ex. 1 & Ex. 11 | Ex. 2 & Ex. 21 | Ex. 3 & Ex. 31 | Ex. 4 & Ex. 41 |
|---|---|---|---|---|---|---|---|---|
| c) | t (Wall), in | 0.055 | 0.065 | 0.075 | 0.1 | 0.14 | 0.14 | 0.18 |
| d) | L (Length), in | 3.05 | 3.05 | 3.05 | 3.05 | 3.75 | 4.75 | 4.75 |
| e) | Tube Vol, in$^3$ | 0.21607 | 0.26158 | 0.30901 | 0.43597 | 1.22051 | 1.54598 | 1.65405 |
| f) | Fill Vol, in$^3$ | 6.1024 | 6.1024 | 6.1024 | 6.1024 | 15.256 | 24.409 | 36.614 |
| g) | Fill Vol, ml | 100 | 100 | 100 | 100 | 250 | 400 | 600 |
| h) | r (=ID/2), in | 0.1775 | 0.1775 | 0.1775 | 0.1775 | 0.3 | 0.3 | 0.3 |
| i) | R (=OD/2), in | 0.2772 | 0.2772 | 0.2772 | 0.2772 | 0.44 | 0.44 | 0.48 |
| j) | t/r | 0.30986 | 0.36620 | 0.42254 | 0.56338 | 0.46667 | 0.46667 | 0.6 |
| k) | t/R | 0.23656 | 0.26804 | 0.29703 | 0.36036 | 0.31818 | 0.31818 | 0.375 |
| l) | Fill Vol/Tube Vol | 28.2427 | 23.3290 | 19.7482 | 13.9973 | 12.4997 | 15.7887 | 22.1360 |

The relationship of the pressures at the Fill Volumes per the Inflation/Deflation Curves Procedure to the Operating Pressures was demonstrated by duplicating the filling part of the Procedure to the Fill Volume with a new (previously unexpanded) set of Ex. 11, 21, 31, and 41 tubes, which are identified as Ex. 11A, 21A, 31A, and 41A, and then modifying the Procedure to allow 24 hours to lapse. Once the pressures were recorded approximately 1 minute after reaching their Fill Volume, the tubes retained these Fill Volumes for approximately 24 hours, then the pressures at the Fill Volume were recorded again and the emptying part of the Procedure was subsequently followed. As the results given in Table 9 show, all the after 24 hours Fill Volume pressures were lower than the after 1 minute Fill Volume pressures by 30-34%. Comparing Table 9 to Table 6 values indicates that the 24 hour delay also results in lower pressures as liquid is removed.

TABLE 9

| | Pressure, PSI for: Reservoir Tube | | | | | | | |
|---|---|---|---|---|---|---|---|---|
| | Ex. 11A | | Ex. 21A | | Ex. 31A | | Ex. 41A | |
| | Tube Exterior Dimensions | | | | | | | |
| | 0.555" OD × 3.05" L | | 0.880" OD × 3.75" L | | 0.880" OD × 4.25" L | | 0.960" OD × 4.25" L | |
| | Wall thickness | | | | | | | |
| | 0.10" | | 0.14" | | 0.14" | | 0.18" | |
| Vol, ml | to Fill Vol | After 24 hrs | to Fill Vol | After 24 hrs | to Fill Vol | After 24 hrs | to Fill Vol | After 24 hrs |
| 0 | 0 | 0 | 0 | 0 | 0 | 0 | 0 | 0 |
| 25 | 13.61 | 7.56 | 14.60 | 6.33 | 15.86 | 5.06 | 18.21 | 6.06 |
| 50 | 13.3 | 6.98 | 14.72 | 6.91 | 14.76 | 6.27 | 18.45 | 8.14 |
| 75 | 15.28 | 7.35 | 14.37 | 6.50 | 13.81 | 6.09 | 17.34 | 8.14 |
| 100 | 17.14 | 12.01 | 13.83 | 6.38 | 13.38 | 5.94 | 16.53 | 7.86 |
| 125 | | | 13.86 | 6.66 | 13.10 | 5.75 | 16.06 | 7.54 |
| 150 | | | 14.09 | 6.91 | 12.86 | 5.82 | 15.75 | 7.20 |
| 175 | | | 14.54 | 6.94 | 12.68 | 5.99 | 15.47 | 7.19 |
| 200 | | | 14.93 | 7.37 | 12.57 | 5.88 | 15.41 | 7.21 |
| 225 | | | 15.32 | 8.30 | 12.62 | 5.86 | 15.34 | 7.18 |
| 250 | | | 15.84 | 10.71 | 12.76 | 6.02 | 15.20 | 7.40 |
| 275 | | | | | 12.92 | 6.27 | 15.34 | 7.23 |
| 300 | | | | | 13.01 | 6.48 | 15.47 | 7.51 |
| 325 | | | | | 13.09 | 6.71 | 15.66 | 7.40 |
| 350 | | | | | 13.28 | 7.34 | 15.87 | 7.50 |
| 375 | | | | | 13.57 | 8.51 | 15.35 | 7.64 |
| 400 | | | | | 13.90 | 9.36 | 15.75 | 7.86 |
| 425 | | | | | | | 16.05 | 8.10 |
| 450 | | | | | | | 16.32 | 8.64 |
| 475 | | | | | | | 16.61 | 8.90 |
| 500 | | | | | | | 16.89 | 9.57 |
| 525 | | | | | | | 17.14 | 9.99 |
| 550 | | | | | | | 17.41 | 10.76 |
| 575 | | | | | | | 17.66 | 11.81 |
| 600 | | | | | | | 17.90 | 12.36 |

Comparison of the Operating Pressures of Table 4 to the after 24 hour Fill Volume pressures of Table 9 for tubes of like structural parameters leads to the conclusion that these pressures are essentially the same. A factor that may account for the slightly higher Operating Pressure values of the Examples of Table 4 compared to the after 24 hour Fill Volume pressures of Table 9, in addition to possible inherent variations of the individual samples themselves, was the presence of a confining non-stretchable housing as described in U.S. Pat. No. 5,284,481 around the tubes for Table 4 examples, while the tubes of Table 9 lacked such a housing. Such a confining housing was also present for all the examples and samples used for Table 1, 3, and 5, while the examples of Table 6, 9, and 10 lacked a confining housing around the tubes.

The Inflation/Deflation Curves Procedure was also used to see if overfilling of the reservoirs would cause insufficient constricting forces in the expanded tube to expel the final amounts of liquid. An unexpanded tube Ex. 11B with structural parameters like those of Ex. 1, 11 and 11A was filled to a Fill Volume of 200 ml according to the Inflation/Deflation Curves Procedure used to generate the values of Table 9 (with a 24 hour delay after reaching the Fill volume). The results are given in Table 10 and show that, for this tube, the structural parameters are adequate to provide sufficient constricting forces to expel all the filled liquid. Comparing the "to Fill Vol" values up to 100 mls for this Ex. 11B to those of Ex. 11A (Table 9) and Ex. 11 (Table 6) shows there is a range in measured pressures that is most likely due to sample variability (all these tubes have the same structural parameters): 12.09 psig for Ex. 11B, 17.14 psig for Ex. 11A, and 18.11 psig for Ex. 11. The ratio of Fill Volume of 200 ml/Tube Vol is approximately 28.

TABLE 10

| | Pressure, PSI for: | |
|---|---|---|
| Reservoir Tube | Ex. 11B | |
| Tube Exterior Dimensions | 0.555" OD × 3.05" L | |
| Wall thickness | 0.10" | |

| Vol, ml | to Fill Vol | After 24 hrs |
|---|---|---|
| 0 | 0 | 0 |
| 25 | 12.53 | 6.56 |
| 50 | 11.92 | 5.25 |
| 75 | 11.79 | 5.03 |
| 100 | 12.09 | 5.35 |
| 125 | 12.77 | 6.28 |
| 150 | 13.41 | 7.13 |
| 175 | 14.00 | 8.33 |
| 200 | 14.53 | — |

Comparative examples that further support the unique criteria of the invention are found from U.S. Pat. No. 7,704,230; such comparative examples use reservoirs made of silicone that match the material parameters of the invention, yet their structural parameters are different from those found to be acceptable for the invention. Within U.S. Pat. No. 7,704,230 are descriptions of certain silicone reservoirs made of NUSIL 4025 that are understood to have cylindrical tube shapes that "hold about 300 milliliters". These reservoirs are stated to have the following dimensions: Comp. Ex. 1 has "a preferred axial length of about 3.5 inches, a preferred outer diameter of about 0.130 inches and a preferred inner diameter of about 0.080 inches"; Comp. Ex. 2 and Comp. Ex. 3 each "preferably has a wall with a thickness of about 0.063 inches" and is presumed to have the same axial length and either the inner or the outer diameter of Comp. Ex. 1. Calculations for structural parameters and ratios like those of Table 8 are made for these comparative examples based on these stated dimensions; these are listed in Table 11. An additional comparative example, Comp. Ex. 4, is given with an axial length of 3.5 inches and an inner diameter of 0.080 inches but with a wall thickness of 0.0315 inches (half of 0.063 inches).

TABLE 11

| item | | Comp. Ex. 1 | Comp. Ex. 2 | Comp. Ex. 3 | Comp. Ex. 4 |
|---|---|---|---|---|---|
| a) | ID, in | 0.080 | 0.080 | 0.004 | 0.08 |
| b) | OD, in | 0.130 | 0.206 | 0.130 | 0.143 |
| c) | t (Wall), in | 0.025 | 0.063 | 0.063 | 0.0315 |
| d) | L (Length), in | 3.50 | 3.50 | 3.50 | 3.50 |
| e) | Tube Vol, in$^3$ | 0.115 | 0.396 | 0.186 | 0.154 |
| f) | Fill Vol, in$^3$ | 18.31 | 18.31 | 18.31 | 18.31 |
| g) | Fill Vol, ml | 300 | 300 | 300 | 300 |
| h) | r (=ID/2), in | 0.040 | 0.040 | 0.002 | 0.040 |
| i) | R (=OD/2), in | 0.0625 | 0.103 | 0.0625 | 0.0715 |
| j) | t/r | 0.625 | 1.575 | 31.5 | 1.575 |
| k) | t/R | 0.400 | 0.612 | 1.008 | 0.881 |
| l) | Fill Vol/Tube Vol | 159.217 | 46.185 | 98.573 | 118.464 |

Referring again to FIGS. 6 and 7, it appears the tubes generally follow Hooke's law between zero pressure and a yield point above the designed operating pressure for the infusion pump (i.e., 6 psi). This Hooke's law behavior is observed for both the inflation profile and the deflation cycle profile. For the present invention, the more important yield point is a "deflation yield point" that appears at about 7 to 8 psi in the deflation portion of the inflation/deflation cycle for all sizes of the infusion pumps (i.e., 100 ml to 400 ml).

With reference to FIGS. 6 and 7 as well as Table 6, the plot of pressure versus volume during inflation of "Ex. 11 to fill" illustrates that pressure of fluid in the inflatable elastomeric tube increases in a substantially linear manner from zero to an inflation yield point (at about 13.4 psig) that is above the target operating pressure (about 6 psig) as the volume increases from 0 milliliters to a volume of about 25 milliliters. As another example, the plot of pressure versus volume during inflation of "Ex. 41 to fill" illustrates that pressure of fluid in the elastomeric tube increases in a substantially linear manner from zero to an inflation yield point (at about 18.5 psig) that is above the target pressure (about 6 psig) as the volume increases from 0 milliliters to a volume of about 25 milliliters.

Once the pressure exceeds the inflation yield point, the pressure-volume relationship is generally non-linear. That is, as the volume of the fluid in the inflatable elastomeric tube increases, the pressure of the fluid in the inflatable elastomeric tube has a less predictable response and will increase or decrease with changes in volume changes. This response is non-Hookean (i.e., does not follow Hooke's law) and is attributed to stretching and deformation of the inflatable tube. As can be seen from FIGS. 6 and 7, the plot of pressure versus volume during inflation of "Ex. 11 to fill" illustrates that pressure of fluid in the inflatable elastomeric tube increases in a generally non-linear manner from the inflation yield point (at about 13.4 psig) to the end of the inflation cycle as the volume increases from about 24 milliliters to a volume of about 100 milliliters. As another example, the plot of pressure versus volume during inflation of "Ex. 41 to fill" illustrates that pressure of fluid in the elastomeric tube responds in a generally non-linear manner from the inflation yield point (at about 18.5 psig) to the end of the inflation cycle as the volume increases from about 15 milliliters to a volume of about 600 milliliters.

During deflation of the inflatable elastomeric tube, the pressure-volume relationship is generally non-linear until the pressure decreases below a deflation yield point. For example, the plot of pressure versus volume during deflation of "Ex. 11 from fill" illustrates that pressure of fluid in the inflatable elastomeric tube decreases in a generally non-linear manner from the end of the inflation cycle/beginning of the deflation cycle to the deflation yield point (at about 8 psig) as the volume decreases from about 100 milliliters to a volume of about 25 milliliters. As another example, the plot of pressure versus volume during deflation of "Ex. 41 from fill" illustrates that pressure of fluid in the elastomeric tube responds in a generally non-linear manner from the end of the inflation cycle/beginning of the deflation cycle to the deflation yield point (at about 7.8 psig) as the volume decreases from about 600 milliliters to a volume of about 25 milliliters.

Referring to "Ex. 11 from fill" and to "Ex. 41 from fill", as the pressure decreases below the deflation yield point, the pressure and volume decrease in a substantially linear relationship until the volume decreases to 0 ml. It is believed that providing a deflation yield point that is above the target operating pressure of the infusion pump allows for the reliable and generally complete evacuation or depletion of the contents of the infusion pump.

Accordingly, the improved elastomeric pump can be described as an infusion pump providing a modified hysteresis profile with a deflation yield point that is above the target operating pressure of the pump. The additional thickness (>0.100") and choice of material (NuSil 4025A) in the inflatable tube provides an extended range of Hooke's law response which is important in providing a uniform flow rate—particularly at low volumes associated with depletion of the pump contents. Normally, the silicone elastomer (even NuSil 4025A) is non-Hookean as elasticity is stress dependent which can readily be seen in the other portions of the inflation-deflation profile.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. An elastomeric pump for an infusion assembly, the pump comprising:
   a mandrel comprising a generally cylindrical body having first end and an opposed second end, a length, a generally uniform outer diameter that corresponds to a first radius ($R_{mandrel}$), a central bore extending through the length, a first port positioned between the first end and second end and extending from the outer diameter to the bore to provide a fluid passageway, a fill port at about the first end in fluid communication with the bore, and exit port at about the second end in fluid communication with the bore; and
   an inflatable elastomeric tube disposed concentrically about the mandrel, the tube positioned between the first end and second end of the mandrel and covering the first port, the tube being sealingly secured on the mandrel near the respective ends of the tube and having an original inner diameter that corresponds to a second radius (r) so that it approximately matches the outer diameter of the mandrel ($R_{mandrel}$), a length (L) less than the length of the mandrel, a wall thickness (t) such that:

$(0.4225 \times r) < t \leq (0.660 \times r)$.

2. The pump of claim 1, wherein the the inflatable tube further comprises a volume ($v_{tube}$) of an elastomeric material:

$v_{tube} = \pi L(2rt + t^2)$.

3. The pump of claim 1 or 2, wherein the introduction of a volume of liquid ($v_{liquid}$) determined according to the following equation:

$(12.50 \times v_{tube}) \leq v_{liquid} \leq (22.16 \times v_{tube})$ through the fill port at a fill pressure of greater than 0 and less than 35 psig expands the inflatable elastomeric tube between the mandrel and the elastomeric tube such that the pump subsequently dispenses substantially all the volume of liquid through the first port upon contraction of the tube to substantially its original inner diameter. pg,33

4. The pump of claim 1, wherein the elastomeric material is an elastomeric silicone.

5. The pump of claim 4, wherein the elastomeric silicone has a Shore Hardness of from about 25 A to about 40 A.

6. The pump of claim 1, wherein the inflatable tube is made from an elastomeric silicone such that the inflatable tube has a Shore Hardness of about 37 A.

7. An elastomeric pump for an infusion assembly, the pump comprising:
   a mandrel comprising a generally cylindrical body having first end and an opposed second end, a length, a generally uniform outer diameter that corresponds to a first radius ($R_{mandrel}$), a central bore extending through the length, a first port positioned between the first end and second end and extending from the outer diameter to the bore to provide a fluid passageway, a fill port at about the first end in fluid communication with the bore, and exit port at about the second end in fluid communication with the bore; and
   an inflatable elastomeric tube disposed concentrically about the mandrel, the tube positioned between the first end and second end of the mandrel and covering the first port, the tube being sealingly secured on the mandrel near the respective ends of the tube and having an original inner diameter that corresponds to a second radius (r) so that it approximately matches the outer diameter of the mandrel ($R_{mandrel}$), a length (L) less than the length of the mandrel, a wall thickness (t) such that:

$(0.4225 \times r) < t \leq (0.660 \times r)$ the inflatable tube further comprising a volume ($v_{tube}$) of an elastomeric material:

$v_{tube} = \pi L(2rt + t^2)$ such that introduction of a volume of liquid ($v_{liquid}$) determined according to the following equation:

$(12.50 \times v_{tube}) \leq v_{liquid} \leq (22.16 \times v_{tube})$ through the fill port at a fill pressure of greater than 0 and less than 35 psig expands the inflatable elastomeric tube between the mandrel and the elastomeric tube such that the pg,34 pump subsequently dispenses substantially all the volume of liquid through the first port upon contraction of the tube to substantially its original inner diameter.

8. An elastomeric pump for an infusion assembly, the pump comprising:
   a mandrel comprising a generally cylindrical body having first end and an opposed second end, a length, a generally uniform outer diameter that corresponds to a first radius ($R_{mandrel}$), a central bore extending through the length, a first port positioned between the first end and second end and extending from the outer diameter to the bore to provide a fluid passageway, a fill port at about the first end in fluid communication with the bore, and exit port at about the second end in fluid communication with the bore; and
   an inflatable elastomeric tube disposed concentrically about the mandrel, the tube positioned between the first end and second end of the mandrel and covering the first port, the tube being sealingly secured on the mandrel near the respective ends of the tube and having an original inner diameter that corresponds to a second radius (r) so that it approximately matches the outer diameter of the mandrel ($R_{mandrel}$), a length (L) less than the length of the mandrel, a wall thickness (t) such that:

$(0.4225 \times r) < t \leq (0.660 \times r)$ and wherein the pump, upon inflation with a predetermined volume of liquid and during delivery of that liquid, exhibits a substantially linear pressure versus volume curve from a deflation yield point that is above a predetermined operating pressure to a volume that corresponds with the dispensing of substantially all the volume of liquid through the first port upon contraction of the tube to substantially its original inner diameter.

9. The pump of claim 8, wherein the the inflatable tube further comprises a volume ($v_{tube}$) of an elastomeric material:

$$v_{tube} = \pi L(2rt + t^2).$$

10. The pump of claim 8 or 9, wherein the introduction of a volume of liquid ($v_{liquid}$) determined according to the following equation: pg,35

$$(12.50 \times v_{tube}) \leq v_{liquid} \leq (22.16 \times v_{tube})$$

through the fill port at a fill pressure of greater than 0 and less than 35 psig expands the inflatable elastomeric tube between the mandrel and the elastomeric tube such that the pump subsequently dispenses substantially all the volume of liquid through the first port upon contraction of the tube to substantially its original inner diameter.

11. The pump of claim 8 or 9, wherein the elastomeric material is an elastomeric silicone.

12. The pump of claim 11, wherein the elastomeric silicone has a Shore Hardness of from about 25 A to about 40 A.

13. The pump of claim 12, wherein the elastomeric silicone has a Shore Hardness of from about 35 A to about 40 A.

14. The pump of claim 13, wherein the inflatable tube is made from an elastomeric silicone such that the inflatable tube has a Shore Hardness of about 37 A.

* * * * *